United States Patent [19]

Hintz et al.

[11] Patent Number: 5,674,707
[45] Date of Patent: Oct. 7, 1997

[54] PRODUCTION OF HETEROLOGOUS PROTEINS IN FILAMENTOUS FUNGI

[75] Inventors: William E. Hintz, Scarborough; Peter A. Lagosky, Toronto, both of Canada

[73] Assignee: Gist-Brocades N.V., Delft, Netherlands

[21] Appl. No.: 470,958

[22] Filed: Jun. 6, 1995

Related U.S. Application Data

[63] Continuation of Ser. No. 321,474, Oct. 11, 1994, which is a continuation of Ser. No. 988,778, Dec. 10, 1992, abandoned.

[51] Int. Cl.⁶ .......................... C12N 15/09; C12N 15/63; C12N 1/15; C07H 21/04
[52] U.S. Cl. ................ 435/69.1; 435/320.1; 435/254.11; 435/172.3; 536/24.1
[58] Field of Search .................. 435/320.1, 69.1, 435/172.3, 254.3, 254.11; 536/24.1

[56] References Cited

FOREIGN PATENT DOCUMENTS

| 2024448 | 3/1991 | Canada . |
|---|---|---|
| WO 86/06097 | 10/1986 | WIPO . |
| WO 94/04673 | 3/1994 | WIPO . |

OTHER PUBLICATIONS

Hintz et al. (1993) Bio/Technology 11:815–818.
P. Kulmburg et al. "Specific binding sites in the alcR . . ." Molecular Microbiology (1993) 7(6), pp. 847–857.
D.W. Griggs et al. "Regulated expression of the GAL4 . . ." Proc. Natl Acad. Sci. USA vol. 88, Oct. 1991, 8597–8601.
Ward, M. "Aspergilus nidulans and other filamentous . . ." Modern Microbial Genetics, 1991, Wiley–Liss, Inc., pp. 455–495.
Gwynne, D.I. et al. "Genetically engineered secretion . . ." Biotechnology, 5(1987), pp. 713–719.
Buxton, et al. "Cloning of the structural gene . . ." Mol Gen Genet, 190 (1983), pp. 403–405.
Royer, J.C. et al. "Analysis of a high frequency transformation . . ." Mol Gen Genet, 225 (1991), pp. 168–176.
R. Lockington et a. "Regulation of alcR, the positive . . ." Molecular Microbiology (1987) 1(3), pp. 275–181.
D.I. Gwynne et al. "Comparison of the cis–acting control regions . . ." Gene 31 (1987), Elsevier Science Publishers (Biochemical Div.), pp. 205–216.
B. Belenbok et al. "Regulation of Genes Involved . . ." Proceedings of the EMBO, Helsinki, 1989, pp. 73–83.
P. Kulmburg et al. "Specific binding sites for the activator. . ." The Journal of Biological Chemistry, vol. 267, No. 29, 1992 Oct. 15 issue, pp.21146–21153.
Molecular Biology of Filamentous Fungi, Proceedings of the EMBO–Workshop, Berlin, Aug. 24–29, 1991, edited by U. Stahl and P. Tudzynski.
J.O. Nehlin et al. "Control of yeast GAL genes . . ." The EMBO Journal, vol. 10, No. 11, 1991, pp. 3373–3377.
D.J. Gwynne et al. "Current use and continued development of an expression system . . ." Proceedings of the EMBO – Helsinki, 1989, pp. 129–136.
H. V. Baker. "GCRI of *Saccharomyces cerevisiae* encodes a DNA . . ." Proc. Natl. Acad. of Sciences, USA, vol. 88 Nov. 1991, pp. 9443–9447.

*Primary Examiner*—Jasemine C. Chambers
*Assistant Examiner*—Scott D. Priebe
*Attorney, Agent, or Firm*—Nixon & Vanderhye

[57] ABSTRACT

Expression of proteins in filamentous fungal hosts is achieved in the presence of glucose using promoter variants in which creA binding sites are functionally disrupted.

10 Claims, 1 Drawing Sheet

```
      -302                              -167
      GCGGGG--------------------GCGGGG
           changed to:
      GTACTA--------------------GTACTA
``` alcA promoter                    ATG -> coding region

```
                                            Sph1                              -302
CGCAGCTCGG GATAGTTCCG ACCTAGGATT GGATGCATGC GGAACCGCAC GAGGGCGGGG
                                                                              ******

CGGAAATTGA CACACCACTC CTCTCCACGC AGCCGTTCCA AGAGGTACGC GTATAGAGCC

GTATAGAGCA GAGACGGAGC ACTTTCTGGT ACTGTCCGCA CGGGATGTCC GCACGGAGAG

-167           SplI
CCACAAACGA GCGGGGCCCC GTACGTGCTC TCCTACCCCA GGATCGCATC CTCGCATAGC
           ******

.TGAACATCTA TATAAAGACC CCCAAGGTTC TCAGTCTCAC CAACATCATC AACCAACAAT

CAACAGTTCT CTACTCAGTT AATTAGAACA CTTCCAATCC TATCACCTCG CATCAAAATG
        mRNA start                                                           Met
```

Fig. 1

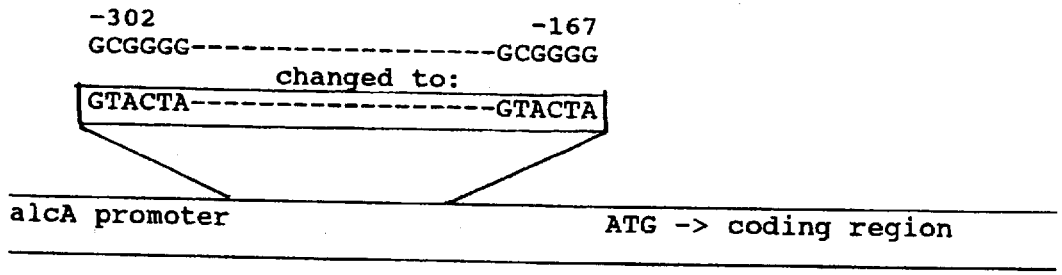

Fig. 2

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCACGAGGGC GGGGCGGAAA TT                    22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ACAAACGAGC GGGGCCCCGT AC                    22

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TATCGATCGC GGGGATCCTC AA                    22

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TGGGCACCGC GGCGAAGGGG AC    22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCGGAAATGC GGGGGGCGGC CA    22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CCAATATAGC CGGGTTTTGT TA    22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AGCCGTTAGC GGGAGGGAAT TT    22

( 2 ) INFORMATION FOR SEQ ID NO:8:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GACTGACTAA GCTTGCATGC GGAACCGCAC GAGGGTACTA CGGAAATTGA C    51

( 2 ) INFORMATION FOR SEQ ID NO:9:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GACTGACTGA ATTCCGTACG GGGTAGTACT CGTTTGTGGC TCTCCGTGCG    50

( 2 ) INFORMATION FOR SEQ ID NO:10:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
CGCAGCTCGG GATAGTTCCG ACCTAGGATT GGATGCATGC GGAACCGCAC GAGGGCGGGG    60
```

( 2 ) INFORMATION FOR SEQ ID NO:11:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CGGAAATTGA CACACCACTC CTCTCCACGC AGCCGTTCCA AGAGGTACGC GTATAGAGCC    60
```

( 2 ) INFORMATION FOR SEQ ID NO:12:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GTATAGAGCA GAGACGGAGC ACTTTCTGGT ACTGTCCGCA CGGGATGTCC GCACGGAGAG    60
```

( 2 ) INFORMATION FOR SEQ ID NO:13:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CCACAAACGA GCGGGCCCC GTACGTGCTC TCCTACCCCA GGATCGCATC CTCGCATAGC    60
```

( 2 ) INFORMATION FOR SEQ ID NO:14:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
TGAACATCTA TATAAAGACC CCCAAGGTTC TCAGTCTCAC CAACATCATC AACCAACAAT    60
```

( 2 ) INFORMATION FOR SEQ ID NO:15:

( i ) SEQUENCE CHARACTERISTICS:
        ( A ) LENGTH: 60 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

CAACAGTTCT CTACTCAGTT AATTAGAACA CTTCCAATCC TATCACCTCG CATCAAAATG    60

PRODUCTION OF HETEROLOGOUS PROTEINS IN FILAMENTOUS FUNGI

This is a Rule 60 continuation of application Ser. No. 08/321,474, filed Oct. 11, 1994, which is a continuation of application Ser. No. 07/988,778, filed Dec. 10, 1992, now abandoned.

FIELD OF THE INVENTION

This invention applies the art of recombinant DNA technology to the production of desired proteins in microbial hosts, particularly the filamentous fungi including Aspergillus species.

BACKGROUND OF THE INVENTION

A variety of gene expression systems have been developed for use with filamentous fungal hosts. Among these are systems that exploit carbon catabolite-repressed promoters, e.g., glucose-repressed promoters, selected primarily because their ability to drive gene expression can be tightly controlled simply by altering fermentation conditions. One system of this type utilizes the promoter of the Aspergillus nidulans alcA gene, which is repressed in the presence of glucose and is induced by ethanol, threonine or related metabolites under glucose-depleted conditions (see Gwynne et al, Biochem. Soc. Trans., 17:338). This dual control offers an attractive, phased approach to fermentation, in which the host Aspergillus strain is first cultured in the presence of glucose to maximize biomass, and is then cultured under glucose-depleted conditions in the presence of inducer, to elicit production of the desired protein. Similarly regulated systems have also been developed, and make use of other glucose-repressed promoters such as the promoter of the aldA gene of Aspergillus nidulans (see Pickett et al, 1987, Gene, 51:217), the amdS gene of Aspergillus nidulans (see Scazzocchio et al, 1992, infra), the gla gene of Aspergillus niger (see Fowler et al, Curr. Genet., 1990,18:537) and the acvA and ipnA genes of Aspergillus nidulans and of Cephalosporium chrysogenum (see Brakhage et al, 1992, 174(11): 3789).

Although the control over gene expression offered by glucose-repressed promoters is desirable in many instances, their use can complicate the production phase of fermentation. For gene product to form, the host strain must be cultured not only under glucose-depleted conditions, but also in a medium that employs a carbon source alternative to the more preferred substrate, glucose. It would accordingly be desirable to develop promoters that are relieved of their glucose-repressed function.

Studies of the glucose-mediated mechanism of carbon catabolite repression in Aspergillus and other filamentous fungi have implicated the product of the creA gene as the principle repressor. It is now widely accepted (see Scazzocchio, in Aspergillus; Biology and Industrial Applications, Butterworth-Heinemann, 1992 at pp.43–63) that when glucose is present, the creA gene product represses expression of genes involved in utilization of other carbon substrates such as ethanol and lactose, and thereby inhibits utilization of those other pathways when glucose is available. Cloning and analysis of Aspergillus nidulans creA has been reported recently by Dowzer and Kelly in Mol. Cell. Biol., 1991, 11(11):5701.

SUMMARY OF THE INVENTION

The domain at which the creA gene product binds within the promoter regions of glucose-repressed filamentous fungal genes has now been identified. This discovery is exploited, in accordance with the present invention, to disrupt the creA binding domain within glucose-repressed promoters, and thereby provide promoter variants that can drive expression in the presence of glucose.

More particularly, and according to one aspect of the invention, there is provided a recombinant DNA expression cassette useful to achieve expression of protein-encoding DNA in a filamentous fungal host, the cassette comprising the protein-encoding DNA and, linked operably therewith, a promoter variant having a creA binding site that is disrupted to permit expression of the protein-encoding DNA in the presence of glucose.

In embodiments of the present invention, the promoter variant is derived from the promoter of an Aspergillus gene involved in ethanol metabolism, selected for example from the alcA, aldA and alcR genes of Aspergillus nidulans.

In another of its aspects, the present invention provides a filamentous fungal strain having incorporated therein a recombinant DNA expression cassette comprising heterologous DNA and, linked operably therewith, a promoter variant having a disrupted creA binding site.

According to another aspect of the invention, there is provided a method for producing a desired protein, which comprises the step of culturing in the presence of glucose a filamentous fungal strain having incorporated therein a recombinant DNA expression cassette comprising DNA coding for the desired protein and, linked operably therewith, a promoter variant having a disrupted and spatially preserved creA binding site.

The invention and its preferred embodiments are now described in greater detail with reference to the accompanying drawings in which:

BRIEF REFERENCE TO THE DRAWINGS

FIG. 1 illustrates the nucleotide sequence of a region (SEQ ID NO'S: 10, 11, 12, 13, 14 and 15) of a region of the Aspergillus nidulans alcA promoter; and FIG. 2 illustrates schematically the construction of an alcA promoter variant.

DETAILED DESCRIPTION OF THE INVENTION AND PREFERRED EMBODIMENTS

The present invention provides a strategy for altering those promoters of filamentous fungal genes that are normally glucose repressed, in order to provide promoter variants that function in the presence of glucose to drive expression of protein-encoding DNA linked operably with the promoter variant. This is achieved by eliminating the creA binding site within the glucose-repressed promoter, either by deletion or more desirably by nucleotide substitution. As used herein, the term "promoter variant" thus refers to a glucose-repressed promoter in which a creA binding site normally resident therein has been disrupted, allowing the promoter variant to function in the presence of a glucose concentration sufficient to sustain growth of a given filamentous fungal strain.

For purposes of the present invention, promoter variants can in principle be developed from the promoter of any glucose-repressed filamentous fungal gene that incorporates within its promoter sequence the creA binding domain. The creA binding domain is characterized as a GC rich motif, and is more particularly identified as a nucleotide region in which at least six G or C residues are incorporated within a contiguous ten nucleotide stretch. The specific sequence of a creA binding domain can vary widely within this parameter, and may for example consist entirely of contiguous G/C residues, e.g., GCGGGGC, or of G/C residues interrupted by one or more A and T residues.

The creA binding domain within a promoter is located typically upstream of each of the required regulatory elements, i.e. the translational and transcriptional start sites. For glucose-repressed filamentous fungal genes having published sequences, identifying the creA binding domain within the promoter will of course be a simple task of locating the GC rich sequence within that sequence. For genes that have been cloned but for which no sequence is yet known, the creA binding domain can be located after sequencing the 5'-untranslated region of the gene, using techniques established in the art. For other glucose-regulated genes, cloning and then sequencing of the 5'-untranslated region thereof will be necessary but can be achieved also according to procedures well established in the art of molecular biology.

From those glucose-repressed promoters incorporating the creA binding domain, promoter variants that are functional in the presence of glucose are obtained by disrupting the creA binding domain. Disruption can be achieved either by wholesale deletion of the creA binding domain and the region 5' thereof, by selective deletion from within the promoter of the creA binding domain or a functional portion thereof, or, more preferably, by replacing one or more of the G/C residues within the creA binding domain. Replacement residues are desirably adenine and thymine. Relative to wholesale and selective deletion, G/C replacement has the advantage of preserving the spatial relationship, and function, of other regulatory domains within the promoter variant. Of course, this can be particularly important in the circumstance where expression regulating regions exist within the promoter at a site upstream of the creA binding site.

In some cases, promoters may contain more than one creA binding site, and it is desirable, in order to eliminate glucose-repression thereof, to disrupt each of the creA binding sites within that promoter. This can be achieved, as just mentioned, either by deleting those sites, by replacing residues within those sites, or by using a combination of these disrupting techniques.

According to specific embodiments of the invention, the promoter variant is a variant of an Aspergillus nidulans promoter identified below, in which the creA binding site noted below is disrupted by nucleotide replacement:

| Gene | 5' flank | creA site | 3' flank | location |
|---|---|---|---|---|
| alcA[1] | GCACGAGG | GCGGGG | CGGAAATT | −302 (SEQ ID NO: 1) |
|  | ACAAACGA | GCGGGG | CCCCGTAC | −167 (SEQ ID NO: 2) |
| aldA[2] | TATCGATC | GCGGGG | ATCCTCAA | −435 (SEQ ID NO: 3) |
|  | TGGGCACC | GCGGCG | AAGGGGAC | −290 (SEQ ID NO: 4) |
| alcR[3] | GCGGAAAT | GCGGGG | GGCGGCCA | −359 (SEQ ID NO: 5) |
| amdS[4] | CCAATATA | GCCGGG | TTTTGTTA | −729 (SEQ ID NO: 6) |
| prnB[5] | AGCCGTTA | GCGGGA | GGGAATTT | −650 (SEQ ID NO: 7) |

[1] = Gwynne et al, Gene, 1987, 51:205
[2] = Picket et al, Gene, 1987, 51:217
[3] = Felenbok et al, Gene, 1988, 73:385
[4] = Scazzocchio et al, 1992, supra
[5] = Sophianopoulou et al, Mol. Microbiol., 1989, 3:705

The creation of promoter variants functional in the presence of glucose can be achieved using these and other promoters by applying now conventional techniques of gene manipulation. For instance, a region of the selected promoter containing the creA binding site can be excised using flanking restriction sites and then incorporated into a vector suitable for amplification and subsequent gene manipulation work. The technique of site-directed mutagenesis can then be applied to disrupt the targetted area binding site. To delete the creA binding site and sequences 5' thereof, for example, an oligonucleotide can be designed which introduces any desired restriction site just 3' of the creA site, to allow excision. The same technique can also be applied to introduce a nucleotide substitution within the creA binding site, using an oligonucleotide that is mismatched at the desired location but which otherwise is complementary to and hybridizes with the region targetted for disruption. The convenient technique of polymerase chain reaction (PCR) can also be applied in combination with the site-directed approach, to mutagenize and then amplify either the entire promoter or a selected region thereof. The desired promoter variant may of course also be synthesized de novo by applying methods now standard in the gene synthesis art. Briefly, this entails the successive 3' to 5' coupling of suitably protected nucleotide reagents in an automated synthesizer, and then the recovery by gel purification of the deprotected polynucleotide. The block ligation approach may be employed, whereby "blocks" of oligonucleotide pairs, up to about 80 nucleotides in length, are synthesized and ligated in correct succession by overhang complementarity, as described for example by Wosnick et al in Gene, 1989, 76:153. In an alternative approach, the desired DNA may be synthesized in toto, and then amplified by the PCR technique, using the strategy disclosed for instance by Barnett et al in Nucl. Acids Res., 1990, 18(10):3094.

Once obtained, the promoter variant may be exploited to drive expression of DNA coding for any desired protein in a filamentous fungal host, in accordance with techniques already otherwise established for the filamentous fungi (for a review see Ballance, Yeast, 1986, 2:229). For this purpose, the present invention provides recombinant DNA constructs in which the promoter variant is linked operably with the protein-encoding DNA. The term "linked operably" means that the promoter is linked with the protein-encoding DNA in a manner enabling expression thereof in the filamentous fungal host. For the purposes of this specification, the protein-encoding DNA is understood to comprise a translational start codon and a translational stop codon; and otherwise encodes either the desired protein end-product per se; a fusion protein in which the desired protein is initially produced in cleavable combination with a carrier protein such as Aspergillus niger glucoamylase; or a secretable precursor in which the desired protein end-product is coupled with a cleavable signal peptide, such as a signal peptide normally associated with an Aspergillus protein e.g. glucoamylase, or any functional equivalent thereof.

In addition to the promoter and the protein-encoding DNA, the constructs of the present invention may also incorporate a transcriptional terminator at a location 3' of the protein-encoding DNA, although experience has shown that such terminators are not essential components of the constructs. Such transcriptional terminators can be obtained as 0.5–1.0 kb fragments of the 3' non-coding regions of Aspergillus genes, for example of the Aspergillus niger glucoamylase gene.

Once the construct is obtained, it can be introduced either in linear form or in plasmid form, e.g., in a pUC-based or other vector, into a selected filamentous fungal host using a technique such as DNA-mediated transformation, electroporation, particle gun bombardment, protoplast fusion and the like. To allow for selection of the resulting transformants, the transformation typically also involves a selectable gene marker which is introduced with the expression cassette, either on the same vector or by co-transformation, into a host strain in which the gene marker is selectable. Various marker/host systems are available, including the pyrG, argB and niaD genes for use with auxotrophic strains of Aspergillus nidulans; pyrG and argB genes for Aspergillus oryzae auxotrophs; pyrG, trpC and niaD genes for Penicillium chrysogenum auxotrophs; and the argB gene for Trichoderma reesei auxotrophs. Dominant selectable markers including amdS, oliC, hyg and phleo are also now available for use with such filamentous fungi as A. niger, A. oryzae, A. ficuum, P. chrysogenum, Cephalosporium acremonium, Cochliobolus heterostrophus, Glomerella cingulata, Fulvia fulva and Leptosphaeria maculans (for a review see Ward in Modern Microbial Genetics, 1991, Wiley-Liss, Inc., at pages 455–495).

Filamentous fungal strains resulting from the transformation are cultured, according to another aspect of the invention, in the presence of a growth-sustaining concentration of glucose, for the purpose of obtaining the desired protein product. Culturing of the strain can be achieved without the need to establish glucose-depleted growth conditions, since the promoter variant driving expression of the desired gene product is no longer functionally repressed in the presence of glucose. For those promoters whose function is otherwise not controlled, production of the desired protein can be achieved throughout the fermentation period. Phased production can also still be achieved, using promoter variants that are controlled by mechanisms other than glucose-repression. As is hereinafter exemplified, the alcA promoter can be functionally controlled, even after disruption of its creA binding site, using an inducing agent to limit protein production to a certain window within the fermentation period.

EXAMPLE 1—Creation of an alcA promoter variant

The promoter of the A. nidulans alcA gene is repressed by a combination of the creA gene product and glucose; it is also induced under glucose-depleted conditions by a combination of the alcR gene product and an inducing agent such as ethanol. To construct an alcA promoter variant that functions in glucose at concentrations sufficient to sustain Aspergillus growth, the alcA promoter was obtained in the manner reported by Gwynne et al in Bio/Technology, 1987, 5:713, and manipulated as described below.

Two putative creA binding sites (both GCGGGGC) were first identified by sequence scanning. As shown in FIG. 1, these sites reside upstream of the ATG initiation codon of the alcA gene at positions −302 and −167, and both are conveniently within a SphI/SplI region of the promoter. To provide an alcA promoter disrupted at these sites by nucleotide replacement, a 160 bp fragment of the promoter was amplified using the tailed primers noted below:

Twenty-five cycles of PCR amplification were performed according to the method reported by Scharf, 1990, In: PCR Protocols: A Guide to Methods and Applicatons. M. A. Innis et al(Eds), Academic Press. The HindIII/EcoRI-tailed amplification product was then sub-cloned into a pTZ18R holding vector and the correct, variant sequence was verified by DNA sequence analysis. The holding vector and the full length alcA gene (pUC8 background) were then each restricted with SphI and SplI, and then selectively ligated to form plasmid Palca$^{var}$-2EB, in which the SphI/SplI region of wild type alcA promoter is replaced with the variant region containing mutations in the two putative creA binding sites. By this approach, spatial arrangement of the nucleotides within the alcA promoter was also conserved.

Because expression from the alcA promoter variant requires induction by the product of the alcR gene which is itself glucose-repressed by a creA-mediated mechanism, an Aspergillus nidulans strain that produces the alcR product in a constitutive manner was exploited for expression of the alcA gene from the variant promoter. The selected host strain was constructed from the Glasgow double auxotroph FGSC4(argB-;ura-) by transforming with a plasmid carrying both the A. nidulans argB gene, as selectable marker, and an expression cassette in which DNA coding for the alcR product (see Felenbok et al, 1989, Gene, 73:385) was placed under expression control of the constitutive promoter of the A. nidulans glyceraldehye-3-phosphate dehydrogenase gene (see Punt et al, 1988, Gene, 69:49. To accomodate multiple copy integration of cassettes carrying the alcA promoter variant, a strain carrying multiple copies of the constitutive alcR gene was chosen, and designated T2625 (ura$^-$, multiple alcR$^c$).

The plasmid palcA$^{var}$-2EB was then introduced into the selected host A. nidulans strain, together with a marker plasmid pFB94 which carries the pyr4 gene of Neurospora crassa (see Buxton and Radford, 1983, Mol. Gen. Genet., 190:403). Transformation was achieved using the PEG/CaCl$_2$-mediated technique according to the protocol reported by Royer et al, 1991, Mol. Gen. Genet., 225:168. Putative transformants, containing the pFB94 construct, were first selected without uridine on minimal medium. Mixed spores collected from approximately 80 ura$^+$ transformants (3 mm colonies) on a single plate were inoculated into 50 ml of selective medium (0.4% 2-deoxyglucose (2-DOG), 1.0% ethanol, 0.67% yeast nutrient broth). The culture was incubated at 30° C. with agitation (200 rpm) for 3 days. Flocculent colonies were collected from the liquid cultures and isolates derived from single spores were prepared from each of the 2-DOG resistant colonies for further analysis.

The host strain and transformants were next cultured for 48 hours at 30° C. in liquid medium containing various supplements selected to examine effects of carbon source on growth. Results are presented in Table 1 below:

(Forward)   HindIII   SphI                    −302
5'GACTGACTAAGCTTGCATGCGGAACCGCACGAGGGTACTACGGAAATTGAC 3' (SEQ ID NO:8)

(Reverse)   EcoRI   SplI                      −167
5'GACTGACTGAATTCCGTACGGGGTAGTACTCGTTTGTGGCTCTCCGTGCG 3' (SEQ ID NO:9)

TABLE 1

| STRAIN | ethanol | glucose/ ethanol | 2-DOG | 2-DOG/ ethanol |
|---|---|---|---|---|
| host | ++ | ++++ | − | − |
| stormed | ++ | ++++ | − | ++ |

Spore suspensions were inoculated into 50 ml of liquid medium supplemented with 0.67% yeast nitrogen base (YNB) and 1 mM uridine; and optionally ethanol (1.0%), glucose (0.4%) or the non-metabolized analogue, 2-deoxyglucose (2-DOG) (0.4%).

As the table indicates, the host strain was able to grow in the presence of either ethanol or glucose, or a combination thereof. It was unable to grow in the presence only of a non-metabolized glucose analogue 2-DOG, nor could it utilize ethanol in the presence of 2-DOG. Clearly, 2-DOG effectively repressed expression from the wild type alcA gene, the product of which is required for ethanol utilization. On the other hand, the palcA$^{var}$-2EB transformants were able to grow in the presence of ethanol when present either in combination with glucose or when present as the sole carbon source (even when glucose or its 2-DOG equivalent were present), demonstrating conclusively that expression of the alcA gene product required for ethanol utilization was mediated by the alcA promoter variant.

We claim:

1. A recombinant DNA construct in which protein-encoding DNA is linked operably with a promoter variant of an Aspergillus promoter, wherein said Aspergillus promoter comprises a creA binding site, which is at least six contiguous guanine or cytosine nucleotides and mediates carbon-catabolite repression of said promoter, and other regulatory sequences; and wherein said promoter variant lacks the creA binding site, comprises the other regulatory sequences, and mediates expression of said protein-encoding DNA in the presence of glucose.

2. The recombinant DNA construct according to claim 1, wherein said creA binding site of said Aspergillus promoter is disrupted by replacement of nucleotide residues in the corresponding site of the promoter variant.

3. The recombinant DNA construct according to claim 2, wherein the nucleotide replacements are selected from adenine and thymidine nucleotides.

4. The recombinant DNA construct according to claim 1, wherein said Aspergillus promoter is selected from the group consisting of alcA, aldA, and AlcR.

5. A filamentous fungal strain having incorporated therein a recombinant DNA construct as defined in claim 1.

6. The filamentous fungal strain according to claim 5, of the genus Aspergillus.

7. The filamentous fungal strain according to claim 6, of the species Aspergillus nidulans.

8. A method for producing a desired protein, comprising the step of culturing in the presence of glucose a filamentous fungus strain as defined in claim 5, thereby producing the desired protein.

9. An Aspergillus nidulans strain that expresses the alcR gene product in the presence of glucose and has incorporated therein a recombinant DNA construct in which protein-encoding DNA is linked operably with a promoter variant of the alcA promoter, wherein said alcA promoter comprises creA binding sites at positions −302 and −167 each with at least six contiguous guanosine or cytosine nucleotides and mediates carbon-catabolite repression of said promoter, and other regulatory sequences; and wherein said promoter variant lacks the creA binding sites, comprises the other regulatory sequences, and mediates expression of said protein encoding DNA in the presence of glucose, whereby the protein-encoding DNA is expressed when said strain is cultured in the presence of glucose and inducer.

10. A method for producing a desired protein, comprising the step of culturing an Aspergillus nidulans strain as defined in claim 9 in the presence of glucose and inducer, thereby producing the desired protein.

* * * * *